(12) United States Patent
Thramann et al.

(10) Patent No.: US 7,828,830 B2
(45) Date of Patent: Nov. 9, 2010

(54) DYNAMIC SPINAL STABILIZATION

(75) Inventors: Jeffery Thramann, Longmont, CO (US); Michael Fulton, Superior, CO (US); Ryan Fredricey, Broomfield, CO (US); Gregory Causey, Broomfield, CO (US); Andrew Lamborne, Golden, CO (US)

(73) Assignee: Lanx, Inc., Broomfield, CO (US)

( * ) Notice: Subject to any disclaimer, the term of this patent is extended or adjusted under 35 U.S.C. 154(b) by 978 days.

(21) Appl. No.: 11/549,675

(22) Filed: Oct. 16, 2006

(65) Prior Publication Data

US 2007/0161997 A1     Jul. 12, 2007

Related U.S. Application Data (63) Continuation-in-part of application No. 11/128,960, filed on May 12, 2005, and a continuation-in-part of application No. 11/128,962, filed on May 12, 2005.

(51) Int. Cl.
*A61B 17/84* (2006.01)
(52) U.S. Cl. .................... 606/331; 606/305; 606/257
(58) Field of Classification Search ................ 606/331
See application file for complete search history.

(56) References Cited

U.S. PATENT DOCUMENTS

| | | | |
|---|---|---|---|
| 4,338,926 A | 7/1982 | Kummer et al. | |
| 4,599,085 A | 7/1986 | Riess et al. | |
| 4,653,481 A | 3/1987 | Howland et al. | |
| 5,005,562 A | 4/1991 | Cotrel | |
| 5,074,864 A | 12/1991 | Cozad et al. | |
| 5,147,359 A | 9/1992 | Cozad et al. | |
| 5,154,718 A | 10/1992 | Cozad et al. | |
| 5,180,393 A | 1/1993 | Commarmond | |
| 5,201,734 A | 4/1993 | Cozad et al. | |
| 5,306,275 A | 4/1994 | Bryan | |
| 5,470,333 A | 11/1995 | Ray | |
| 5,496,318 A | 3/1996 | Howland et al. | |
| 5,531,745 A | 7/1996 | Ray | |
| 5,609,634 A | 3/1997 | Voydeville | |
| 5,645,599 A | 7/1997 | Samani | |
| 5,658,335 A | 8/1997 | Allen | |

(Continued)

FOREIGN PATENT DOCUMENTS

EP     0322334 A1     6/1989

(Continued)

OTHER PUBLICATIONS

International Bureau Notification Concerning Transmittal of International Preliminary Report on Patentability (Chapter I of the Patent Cooperation Treaty) Nov. 27, 2008.

(Continued)

*Primary Examiner*—Eduardo C Robert
*Assistant Examiner*—Julianna N Harvey
(74) *Attorney, Agent, or Firm*—Holland & Hart LLP (57) ABSTRACT

A dynamic spinal stabilization apparatus comprises a stabilization device such as a rod or a plate. Elongated bores, interfaces, or terminations packed with elastic material provides relative movement between the devices to allow spinal flexion and extension. Initially, relative movement may be constrained by a degradable materials, such as a resorbable material, to allow and screws to fuse to the associated bone.

7 Claims, 7 Drawing Sheets

U.S. PATENT DOCUMENTS

| | | | |
|---|---|---|---|
| 5,683,390 A | 11/1997 | Metz-Stavenhagen et al. |
| 5,683,404 A | 11/1997 | Johnson |
| 5,725,582 A | 3/1998 | Bevan et al. |
| 5,800,550 A | 9/1998 | Sertich |
| 5,836,948 A | 11/1998 | Zucherman et al. |
| 6,113,602 A | 9/2000 | Sand |
| 6,135,772 A | 10/2000 | Jones |
| 6,156,040 A | 12/2000 | Yonemura et al. |
| 6,277,094 B1 | 8/2001 | Schendel |
| 6,293,949 B1 | 9/2001 | Justis et al. |
| 6,440,169 B1 | 8/2002 | Elberg et al. |
| 6,451,019 B1 | 9/2002 | Zucherman et al. |
| 6,548,569 B1 | 4/2003 | Williams et al. |
| 6,582,433 B2 | 6/2003 | Yun |
| 6,599,294 B2 | 7/2003 | Fuss et al. |
| 6,626,944 B1 | 9/2003 | Taylor |
| 6,635,060 B2 | 10/2003 | Hanson et al. |
| 6,641,582 B1 | 11/2003 | Hanson et al. |
| 6,652,527 B2 | 11/2003 | Zucherman et al. |
| 6,719,795 B1 | 4/2004 | Cornwall et al. |
| 6,761,720 B1 | 7/2004 | Senegas |
| 6,783,527 B2 | 8/2004 | Drewry et al. |
| 6,800,084 B2 | 10/2004 | Davison et al. |
| 6,824,565 B2 | 11/2004 | Muhanna et al. |
| 6,838,493 B2 | 1/2005 | Williams et al. |
| 7,018,379 B2 | 3/2006 | Drewry et al. |
| 7,029,475 B2 | 4/2006 | Panjabi |
| 2001/0012938 A1 | 8/2001 | Zuckerman et al. |
| 2002/0029039 A1 | 3/2002 | Zucherman et al. |
| 2002/0147449 A1 | 10/2002 | Yun |
| 2002/0156150 A1 | 10/2002 | Williams et al. |
| 2003/0153915 A1 | 8/2003 | Nekozuka et al. |
| 2003/0180266 A1 | 9/2003 | McKay et al. |
| 2003/0187509 A1 | 10/2003 | LeMole, Jr. |
| 2003/0216736 A1 | 11/2003 | Robinson et al. |
| 2003/0225021 A1 | 12/2003 | McKay et al. |
| 2004/0024458 A1 | 2/2004 | Senegas et al. |
| 2004/0059337 A1 | 3/2004 | Hanson et al. |
| 2004/0059339 A1 | 3/2004 | Roehm, III et al. |
| 2004/0106995 A1 | 6/2004 | Le Couedic et al. |
| 2004/0167520 A1 | 8/2004 | Zucherman et al. |
| 2004/0199168 A1 | 10/2004 | Bertagnoli et al. |
| 2004/0225289 A1* | 11/2004 | Biedermann et al. ......... 606/61 |
| 2005/0085812 A1* | 4/2005 | Sherman et al. ............... 606/61 |
| 2005/0136764 A1 | 6/2005 | Sherman |
| 2005/0143737 A1 | 6/2005 | Pafford et al. |
| 2006/0058791 A1* | 3/2006 | Broman et al. ................ 606/61 |
| 2006/0271055 A1 | 11/2006 | Thramann |

FOREIGN PATENT DOCUMENTS

| WO | WO 2004/073533 A1 | 8/2004 |
|---|---|---|
| WO | 2005037110 | 4/2005 |

OTHER PUBLICATIONS

Search Report issued May 13, 2008 for Application No. PCT/US2007/081542.

European Search Report received for 07844324.9 mailed Nov. 11, 2009.

* cited by examiner

FIG.7C

DYNAMIC SPINAL STABILIZATION

CROSS-REFERENCE TO RELATED APPLICATIONS

This application is a continuation in part of U.S. patent application Ser. No. 11/128,960, titled SPINAL STABILIZATION, filed May 12, 2005, incorporated herein by reference as if set out in full, and a continuation in part of U.S. patent application Ser. No. 11/128,962, titled PEDICLE SCREW BASED VERTEBRAL BODY STABILIZATION APPARATUS, filed May 12, 2005, incorporated herein by reference as if set out in full.

FIELD OF THE INVENTION

The present invention relates to spinal stabilization and, more particularly, to a spinous process distraction device that provides both stabilization of the spinal segments as well as movement in both the flexion and extension directions.

BACKGROUND OF THE INVENTION

Surgical techniques to correct or address spinal problems are turning more and more to non-fusion technologies. One type technology involves spinous process stabilization. Spinous process stabilization is further explained in U.S. patent application Ser. No. 11/128,960 filed May 12, 2005, titled SPINAL STABILIZATION. Another similar technology comprises using conventional pedicle screws and a device to maintain distraction of the spinal segment. Pedicle based systems such as this are further described in U.S. patent application Ser. No. 11/128,962, filed May 12, 2005, titled PEDICLE SCREW BASED VERTEBRAL BODY STABILIZATION APPARATUS. The pedicle based system includes pedicle screws threaded into the pedicles of adjacent spinal segments. A rod connecting the two pedicles is provided with a joint or dampener to allow relative movement between the pedicles. The joint or movement is designed to provide increasing resistance to movement to prevent hard or jolting stops at the maximum extension and flexion movements.

Other conventional pedicle based stabilization system includes a pedicle screw platform threaded into at least a superior and inferior pedicle. Stabilizing cords a placed and spacers inserted between sets of pedicle screws. Once everything is placed, the cords are tightened.

Conventional pedicle based systems, such as the one explained above, provide adequate support, however, any flex of the system is abruptly stopped by either the cord or the spacer. Even if the spacer provides for some flex, the cord provides an abrupt stop in the opposite direction.

Instead of the screw, spacer cord based systems, some pedicle screw stabilization devices provide tracks to allow some movement. For example, the spacer may have elongated slots or tracks on the superior and/or inferior end the spacer to move relative to the pedicle screw, which allows for some relative movement between the superior and inferior vertebrae. The track provides more flex than the spacer/cord systems, but provides abrupt stops in both directions.

Against this background, it would be desirous to develop an improved dynamic spinal stabilization device.

SUMMARY OF THE INVENTION

To attain the advantages and in accordance with the purpose of the invention, as embodied and broadly described herein, a pedicle screw based spinal stabilization apparatus is provided. The apparatus uses materials specifically designed to dampen the movement to provide a gentle stop. The apparatus comprises a spinal stabilization device having a first end and a second end. A first bore resides in the first end and a second bore resides in the second end. At leas tone of the first and second bores are elongated. Pedicle screws extend through the bores to couple the device to the vertebral bodies. An elastic material is packed in the elongated bore to allow limited movement between the pedicle screw and the elongated bore. The elastic material provides increasing resistance to movement as it becomes more elastically deformed.

The present invention also provides spinal stabilization device comprising a plurality of pedicle screw anchors to substantially align with a corresponding plurality of vertebral bodies. A plurality of pedicle screws thread into vertebral bodies and connect the plurality of pedicle screw anchors to the plurality. A rod is coupled to and extends between the plurality of pedicle screw anchors. At least one pedicle screw anchors is elongated to provide a space for one of the pedicle screws to move. Elastic material packed in the space provides resistance to movement of the at least one pedicle screw.

The present invention further provides a spinal stabilization device comprising a first pedicle screw anchor and a second pedicle screw anchor coupled to vertebral bodies with a first pedicle screw and a second pedicle screw. A rod extends between the anchors and includes a first rod part coupled to the first pedicle screw anchor and extending from the first pedicle screw anchor towards the second pedicle screw anchor and a second rod part coupled to the second pedicle screw anchor and extending from the second pedicle screw anchor towards the first pedicle screw anchor. A rod interface couples the first rod part and the second rod part, wherein the rod interface allows relative motion between the first rod part and the second rod part.

The present invention further provides a spinal stabilization device comprising a first pedicle screw anchor and a second pedicle screw anchor coupled to vertebral bodies with a first pedicle screw and a second pedicle screw. A rod extends between the anchors and ends in a dynamic termination proximate the first pedicle screw anchor. The dynamic termination allows for relative movement.

The present invention still further provides a spinal stabilization device comprising spinal fusion plate having a first end and a second end opposite the first end. The first end and the second end have a first pair of pedicle screw bore and a second pair of pedicle screw bores respectively. At least one of the pairs of bores resides in an elongated bore. A plurality of elastic struts connect the at least one pair of bores to the elongated bore. The plurality of elastic struts allowing relative movement between at least the first pair of pedicle screw bores or the second pair of pedicle screw bores and the spinal fusion plate.

The foregoing and other features, utilities and advantages of the invention will be apparent from the following more particular description of a preferred embodiment of the invention as illustrated in the accompanying drawings.

BRIEF DESCRIPTION OF THE DRAWINGS

The accompanying drawings, which are incorporated in and constitute a part of this specification, illustrate embodiments of the present invention, and together with the description, serve to explain the principles thereof. Like items in the drawings are referred to using the same numerical reference.

DETAILED DESCRIPTION

The present invention will be described with reference to the Figures. While the present invention is described with reference to use of a stabilization rod or plate connecting vertebrae in the stabilized spinal segment, one of ordinary skill in the art on reading the disclosure will now recognize that other devices could be equally employed to connect the vertebrae of the associated segment. Other devices include, for example, cervical plates, bars, or the like.

Figure 1:
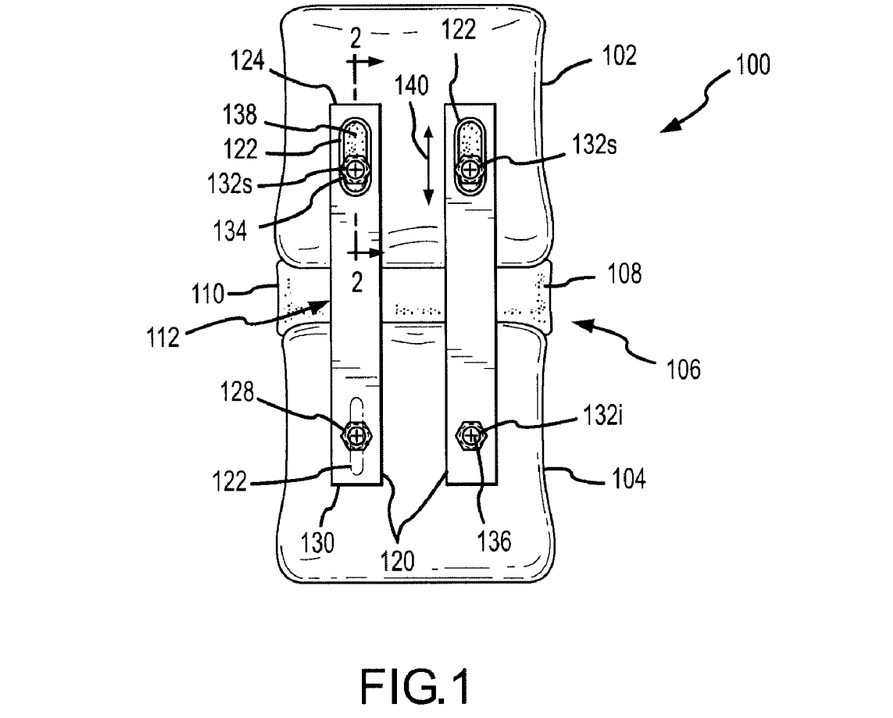
FIG. 1 shows a top plan view of a stabilization device consistent with an embodiment of the present invention.

Referring first to FIG. 1, a spinal segment 100 is shown. Spinal stabilization segment 100 includes a superior vertebral body 102 and an inferior vertebral body 104 separated by an intervertebral disc space 106. Intervertebral disc space 106 is generally occupied by an intervertebral disc 108 having an annulus 110 encapsulating a disc nucleus 112.

Extending between superior vertebral body 102 and inferior vertebral body 104 are two spinal stabilization devices 120. While two spinal stabilization device 120 are shown, more or less could be used. However, parallel devices is relatively conventional in spinal applications. The spinal stabilization devices are identical so only one will be described herein for convenience. Spinal stabilization device 120 may be a cylindrical rod, a square rod, an elliptical rod, or any geometric shape as a matter of design choice. Moreover, a single plate could be used as a substitute for the two bars shown. Spinal stabilization device 120 may be an type of biocompatible material including, for example, titanium, nitinol, other metal alloys, plastics, synthetics, or the like. Spinal stabilization device 120 has at least one elongated bore 122, typically shaped like an oval, but other geometric shapes or random shapes are possible, at a first end 124 of spinal stabilization device 120. Elongated bore 122 defines a slot 126. A bore 128 exists at a second end 130 of spinal stabilization device 120. Bore 128 may be replaced with an elongated bore 122, which is shown in phantom, such that spinal stabilization device has elongated bores 122 at both first end 124 and second end 130.

Pedicle screws 132 are threaded through elongated bore 122 and bore 126 into the pedicles of superior vertebral body 102 and inferior vertebral body 104. For identification, superior pedicle screw is identified as 132s and inferior pedicle screw is designated 132i. Notice, while elongated bore 122 is shown aligned with superior vertebral body 102, it could easily be aligned with inferior vertebral body 104. A nut 134 or coupling device may be threaded onto a head 136 of pedicle screws 132.

Slot 126 is filled with a biocompatible flexible or elastic material 138, such as, a biocompatible resin or electromeric compound, shown by cross-hatch. Elastic material 138 allows relative and limited movement in both a flexion and extension directions as represented by arrow 140. The slot 126 filled with elastic material 138 provides a means to provide stabilized, dampened movement between vertebral bodies. Elastic material 138 could be any number of biocompatible plastics, resins, metals, alloys or the like. For example, elastic material could be an elastomeric polymer such as silicone rubber, polyurethane, SULENE®, available from Sulzer Brothers Limited Corporation, Switzerland. Other materials include springs, spring metal, struts, alloys such as Shaped memory alloys, titanium, or the like.

For example, in this example, spinal stabilization device 120 is fixedly attached to inferior vertebral body 104. As a person flexes, in other words bends over, the inferior vertebral body 104 and superior vertebral body 102 begin to move apart. Spinal stabilization device 120 moves in relation to inferior vertebral body 104. Initially, movement of inferior vertebral body 104 and spinal stabilization device 120 does not influence the movement of superior body 102, which would move in accordance with a conventional flex motion of the person. However, as superior vertebral body 102 moves, pedicle screw 132s to move towards first end 124 of spinal stabilization device 120 in slot 126. Movement of pedicle screw 132s in slot 126 causes compression of elastic material 138. As the compression increases, the resistance of elastic material 138 to further compression increases until further compression is inhibited. At this time, superior and inferior vertebrae would move somewhat in unison via pedicle screws 132 and spinal stabilization device 120. The gradual increase in resistance provides a dampened or gentle stop to the relative movement and causes further movement of vertebral bodies 102 and 104 to be substantially in unison. Extension of would cause a similar reaction in the opposite direction, and the pedicle would relatively move towards second end 130 of spinal stabilization device 120.

As any surgeon would recognize, one difficult with systems providing relative movement is anchoring pedicle screws 132 into vertebral bodies 102 and 104. In systems allowing relative motion, the anchoring of the pedicle screws is exasperated. Elastic material 138 may have incorporated into it material 140 that makes elastic material 138 relatively inelastic. The incorporation of material 140 is best seen in FIG. 2 and explained more fully below.

Ideally, material 140 would decay over time and elastic material 138 would become increasingly more elastic. In other words, material 140 would act as a lock to allow bone growth, for example, to fuse vertebral bodies 102 and 104 with pedicle screws 132. After sufficient time to initiate fusion of the vertebral bodies to the pedicle screws, but prior to fusion of the superior vertebral body 102 and inferior vertebral body, material 140 would begin to decay allowing the relative motion described above. It is envisioned that material 140 would comprise a resorbable material, but any material that is biocompatible and decays over time would be useable. While shown as discrete particles, elastic material and material 140 may form a homogeneous resin or the like. Alternatively, material 140 could form a separate layer of material in bore 122, which is shown in phantom on FIG. 2. The separate layer could reside in the bore proximate the bone interface, opposite the bone interface, or interspersed throughout the bore. Moreover, multiple layers of material are possible.

Packing material 140, such as a resorbable material, into elongated bore 122 provides a contained volume into which material 140 can be placed. Packing material 140 into the contained space allows material 140 to provide a high resistance to movement, which allows pedicles screws to fuse and anchor, but does not require material 140 to resist shear forces. This is useful for resorbable materials as they can provide relatively high compression resistance, but generally have limited or relatively low resistance to shear forces.

Figure 2:
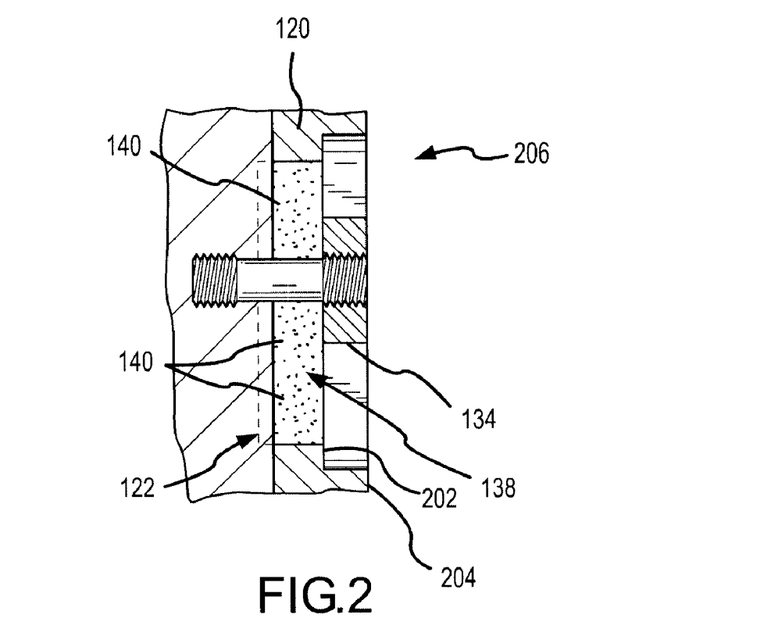
FIG. 2 shows a cross sectional view of the device of FIG. 1.

Referring to FIG. 2, a cross sectional view of an elongated bore 122 is shown. Elongated bore 122 may be designed with a shoulder 202 recessed from a surface 204 of spinal stabilization device 120. Thus, a channel 206 would be formed in surface 204. Nut 134 would rest on shoulder 202 in channel 206 to provide a lower profile for the device.

Figure 3:
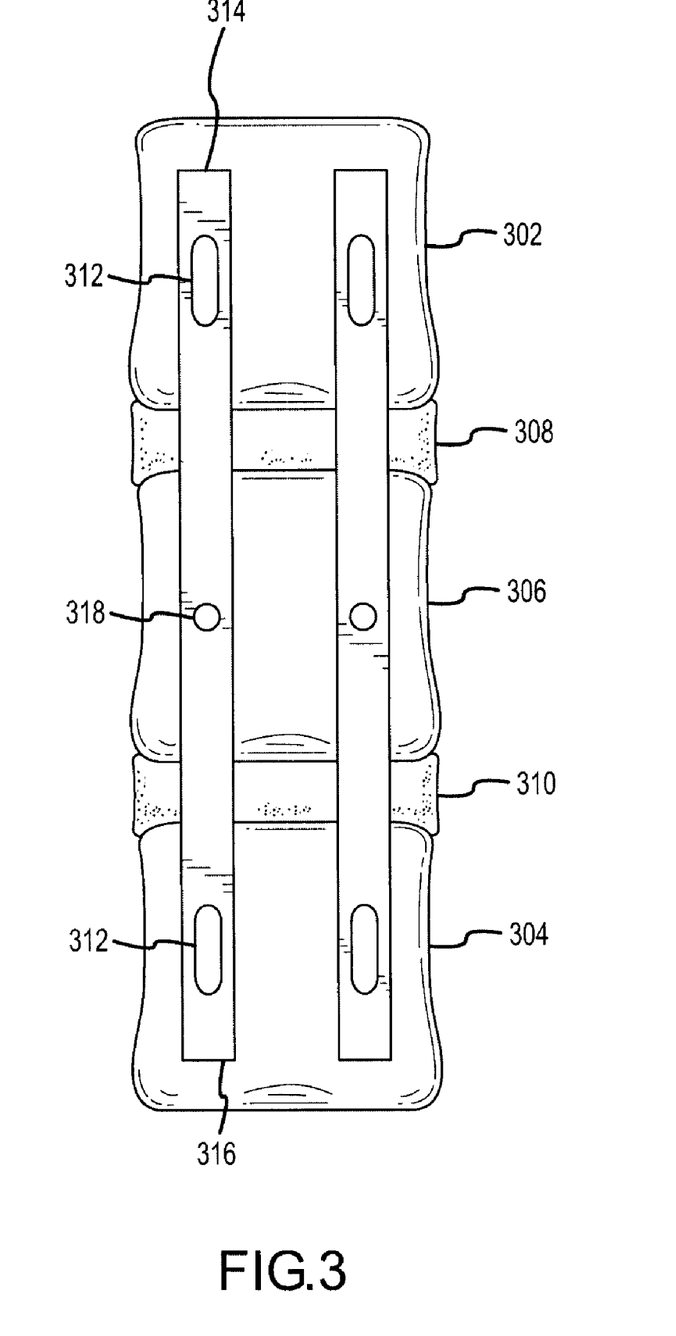
FIG. 3 shows a top plan view of another stabilization device consistent with an embodiment of the present invention.

While FIG. 1 shows two vertebral bodies 102 and 104 separated by one intervertebral disc 108 (also known herein as a single level), one of ordinary skill in the art would recognize the present invention could be use for two, three, or more level device as necessary. FIG. 3, for example, shows spinal stabilization device 300 extending from a superior vertebral body 302 to an inferior vertebral body 304 across an intermediate vertebral body 306. Superior vertebral body 302 is separated from intermediate vertebral body 306 by a superior intervertebral disc space 308 and inferior vertebral body 302 is separated from intermediate vertebral body 306 by inferior intervertebral disc space 310. In this example, an elongated bore 312 resides at both a first end 314 aligned with superior vertebral body 302 and a second end 316 aligned with inferior vertebral body 304. A conventional bore 318 is aligned with intermediate vertebral body 306.

Figure 4:
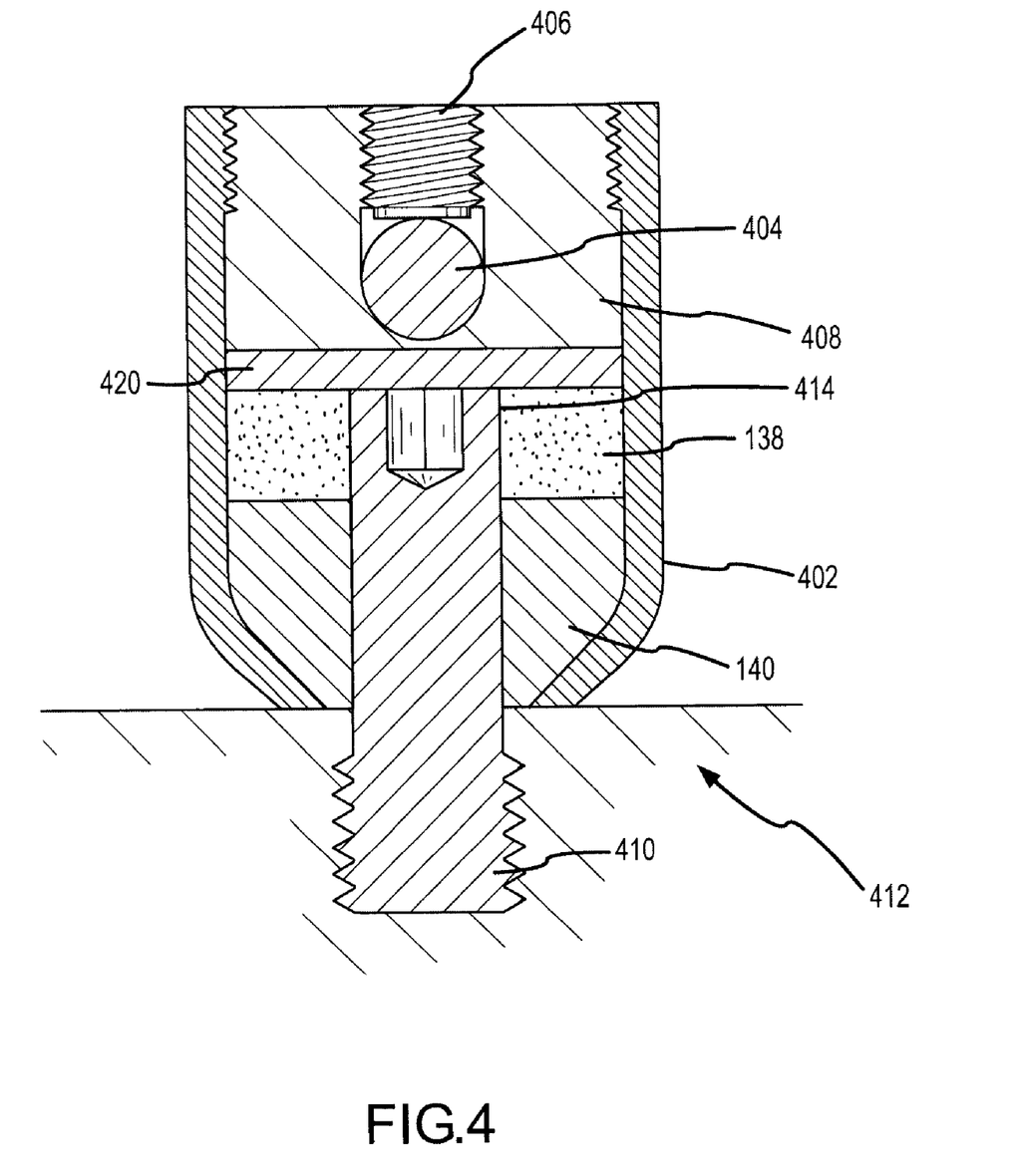
FIG. 4 shows a cross-sectional view of another stabilization device consistent with an embodiment of the present invention.

Referring now to FIG. 4, another embodiment is shown and described. FIG. 4 shows a micro-motion multi-axial pedicles screw anchor 402 containing a rod 404. While shown as multi-axial, anchor 402 does not need to be a multi-axial device. A set screw 406 couples (such as by corresponding threads) into saddle 408 to provide seating force to rod 404. Anchor 402 provides a section with elastic material 138 and material 140 about a pedicle screw 410 threaded into pedicle 412. Pedicle screw 410 has a connector 414 to allow a tool, such as a hex driver, to thread pedicle screw 410 into pedicle 412. Elastic material 138 and material 140 may be any combination of elements as outlined above. A spacer 420, which may simply be an air gap or some non-compressible material, resides between saddle 408 and screw 410. Spacer 420 inhibits the compressive force supplied by set screw 406 from locking pedicle screw 410 in place.

Elastic material 138 provides dampened motion in both the flex and extension directions. Material 140, such as a resorbable or other degradable material, initially restricts the motion until pedicle screw 410 and pedicle 412 fuse. As material 140 degrades, elastic material 138 allows more motion and provides a shock absorbing effect as well.

Figure 5A:
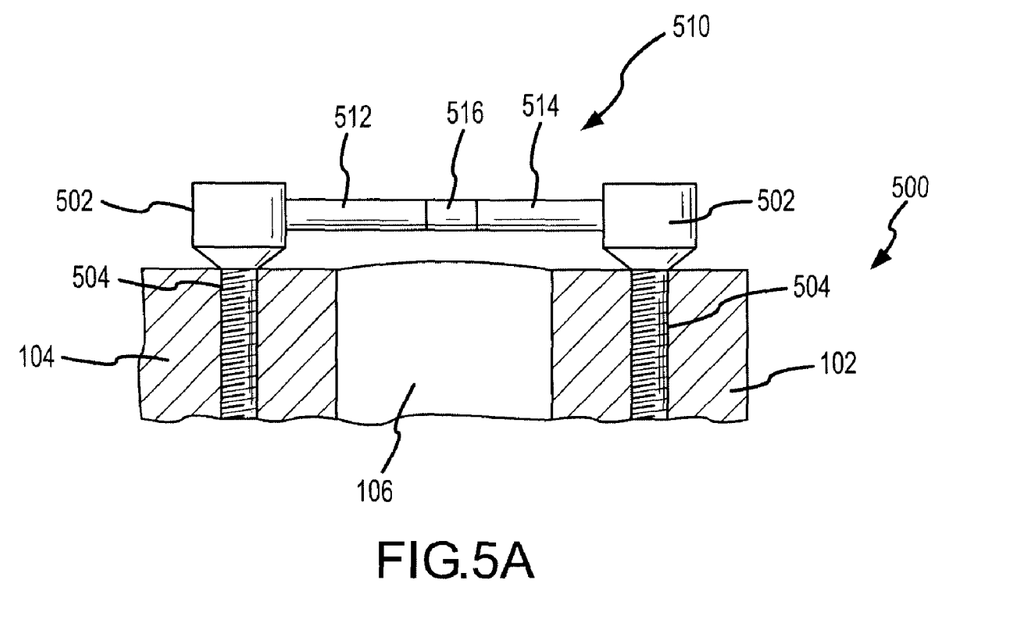
FIGS. 5A and 5B show another stabilization device consistent with an embodiment of the present invention.
Figure 5B:
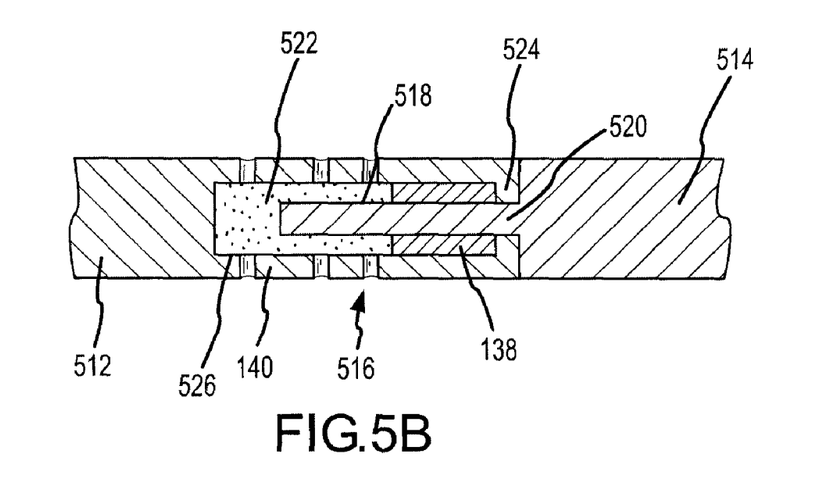

Referring now to FIGS. 5A and 5B, a rod based stabilization device 500 is shown extending across inferior vertebrae 104, superior vertebrae 102 and disc space 106. Rod based stabilization device comprises screw anchors 502 with pedicle screws 504 threaded into superior pedicle 102 and inferior pedicle 104. A rod 510 extends between anchors 502. Anchors 502 and pedicle screws 504 can be any conventional device as known in the art and will not be further explained herein. Rod 510 comprises an inferior rod part 512 and a superior rod part 514. Inferior rod part 512 is coupled to superior rod part 514 by a rod interface 516. Rod interface will be explained with reference to FIG. 5B. While shown as having identical sizes/diameters, inferior rod part 512, superior rod part 514, and rod interface 516 may have different sizes/diameters.

Referring now to FIG. 5B, rod interface 516 is shown in more detail. Rod interface comprises a female socket portion 518 attached to inferior rod part 512 and a male protrusion portion 520 attached to superior rod part 514. Female socket portion 518 could be connected to superior rod part 514 and male protrusion portion 520 could be attached to inferior rod part 512 instead. Female socket portion 518 forms a space 522 that may end in protrusion 524. Space 522 is filled with both elastic material 138 and material 140. Male protrusion portion 520 is fitted in space 522 such that elastic material 138 and, at least temporarily, material 140 couples, bonds, or adherers male protrusion 520 to socket 518. Material 140 being relatively rigid prevents motion, but once degraded, elastic material 138 allows limited motion between male protrusion portion 520 and female socket portion 518, which allows some flex and extension of the spine. To facilitate absorption of material 140, female socket portion 518 may be formed with perforations 526.

Figure 6A:
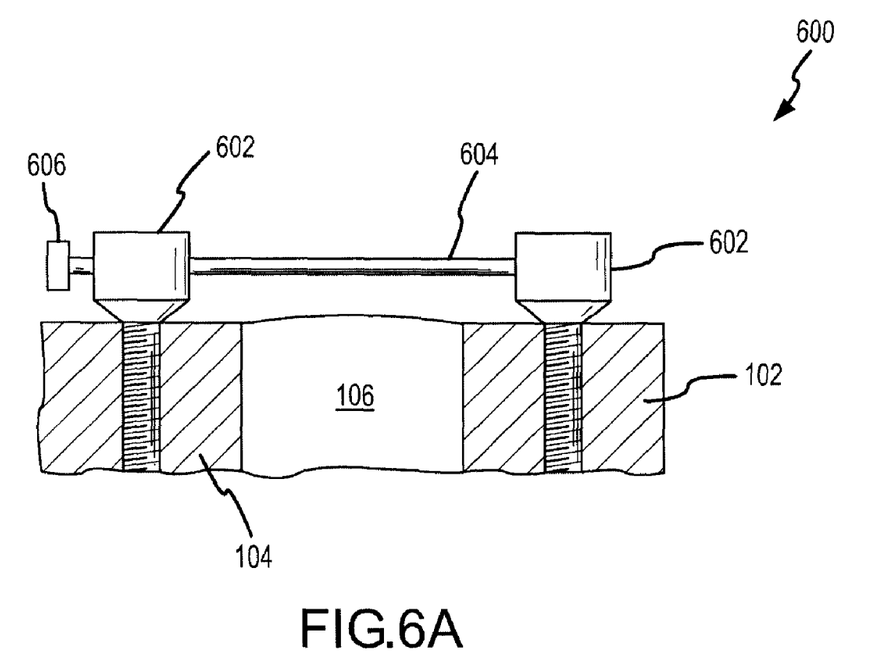
FIGS. 6A-6C show another stabilization device consistent with an embodiment of the present invention.
Figure 6B:
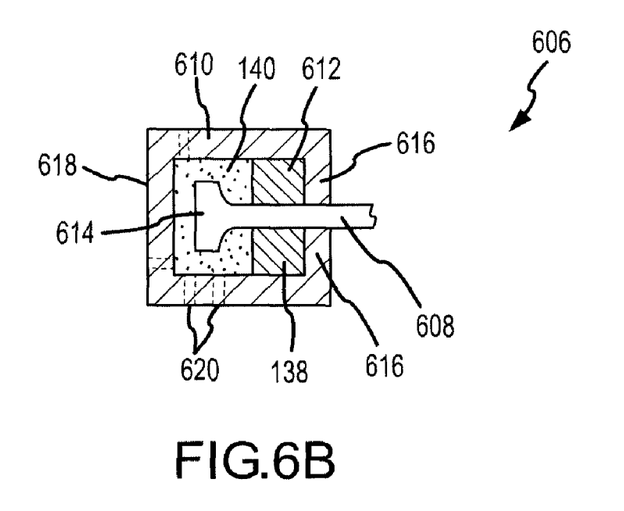

Referring now to FIGS. 6A, 6B, and 6C, another dynamic stabilization device 600 is shown and described. Device 600 includes anchors 602 and a rod 604 with a dynamic termination 606. Rod 604 extends between anchors 602 across inferior vertebrae 104, superior vertebrae 102, and disc space 106. Dynamic termination 606 may reside proximate either the inferior pedicle 104, the superior pedicle 102, or both. As shown in FIG. 6B, dynamic termination 606 includes a male protrusion 608 attached to rod 604. Male protrusion 608 extends into a recess 612 formed by a termination cap 610. Male protrusion 608 may terminate with a protrusion 614, such as a flange or rib, and termination cap 610 may have a protrusion 616, such as shoulders, to inhibit male protrusion 608 from dislodging from termination cap 610. Male protrusion 608 is coupled, bonded, adhered to termination cap 610 by elastic material 138 and material 140 residing in recess 612. Termination cap 610 may have a lid 618 to apply more or less volume associated with recess 612. Termination cap 610 may have perforations 620 to facilitate absorption of material 140.

Figure 6C:
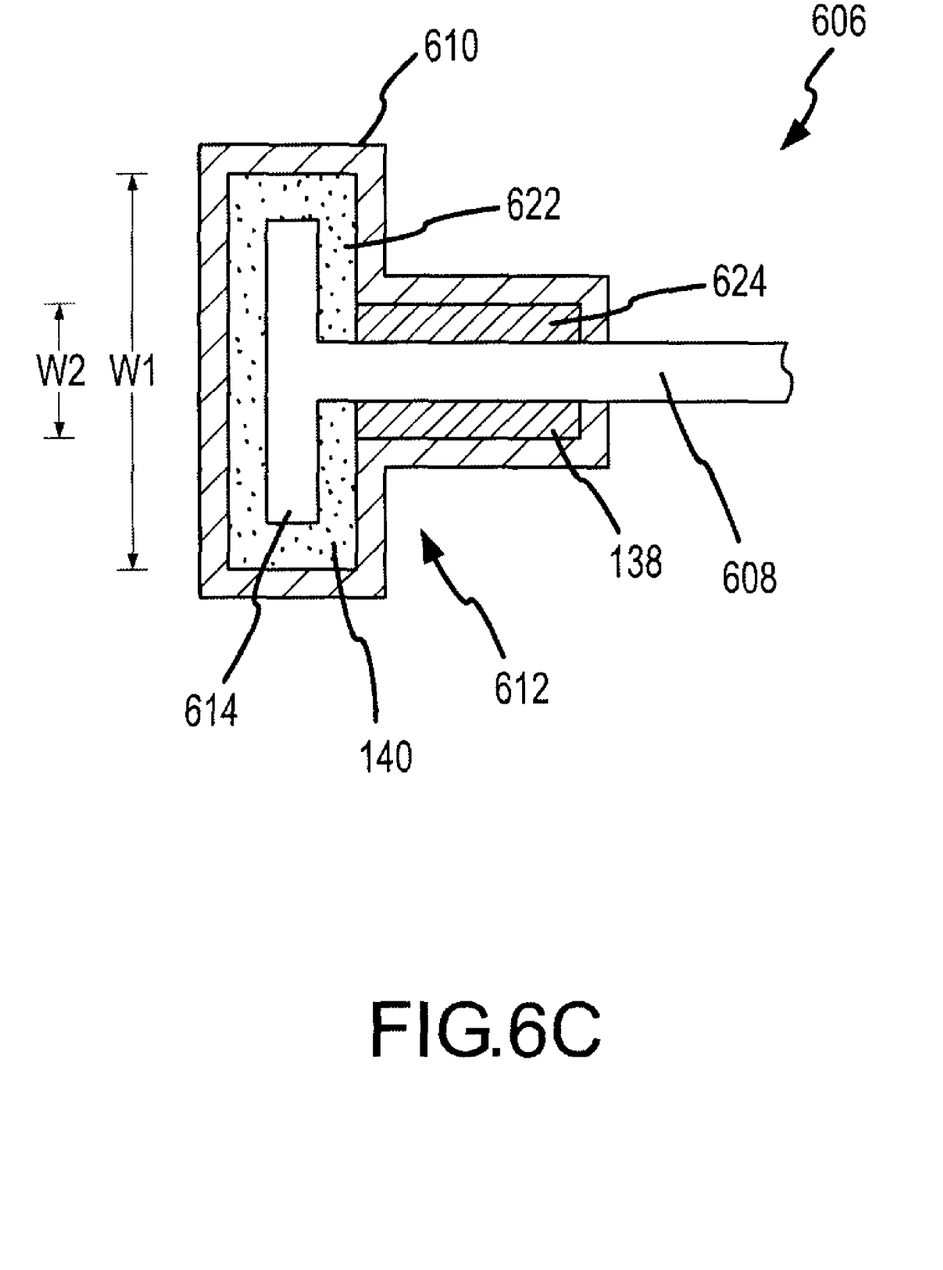

Termination cap 610 may be formed with multiple stages as shown in FIG. 6C. Recess 612 may have a first portion 622 with a first width W1 to hold material 140. Protrusion 614 may reside in first portion 622. Material 140 compressing protrusion 614 would inhibit motion of rod 604. Recess 612 would have a second portion 624 having a second width W2 to hold elastic material 138.

Figure 7A:
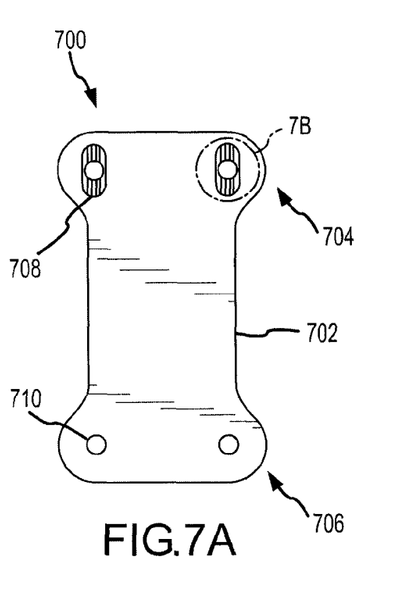
FIGS. 7A, 7B, and 7C show another stabilization device consistent with an embodiment of the present invention.
Figure 7B:
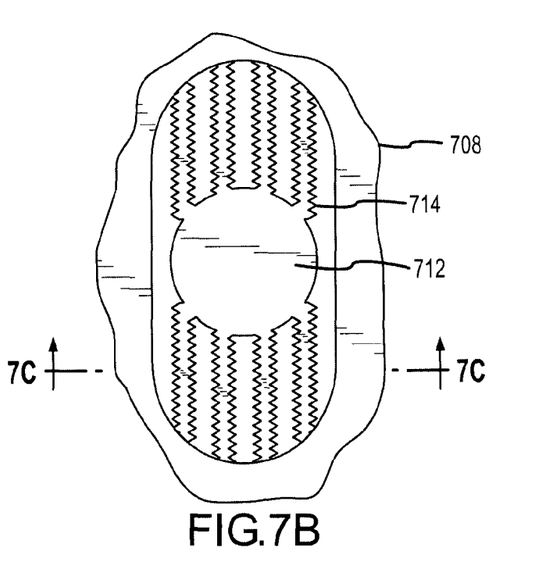
Figure 7C:
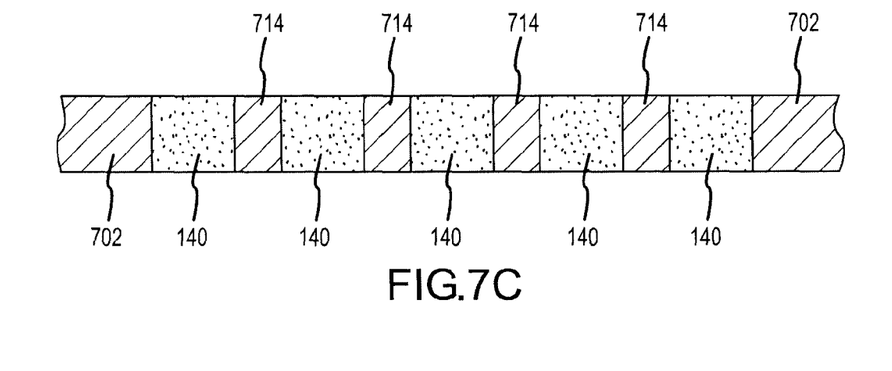

Referring now to FIGS. 7A, 7B, and 7C, another stabilization device 700 is shown and described. Stabilization device 700 comprises a spinal plate 702, such as an anterior cervical plate as shown, having a first end 704 and a second end 706 opposite first end 704. First end 704 is provided with a pair of elongated bores 708. Second end 706 is provided with a pair of conventional bores 710. Conventional bores 710 may be replaced with elongated bores 708. Pedicles screws, not shown, thread through the bores into pedicles to anchor the plate 702. Referring now to FIG. 7B, one elongated bore 708 is shown in more detail. A pedicle screw bore 712 connected to elongated bore 708 by struts 714. Struts 714 may be any of the above mentioned materials or milled into plate 702. While shown with 4 struts 714, more or less struts are possible. The remainder of elongated bore is filled with material 140 to inhibit motion while pedicle screws and pedicles are fusing. Once fused, struts 714 allow limited motion between the vertebrae. Struts 714 are shown with an accordion shape to facilitate elastic movement, but other devices and shapes to allow movement are possible, such as making struts from shaped memory alloys. FIG. 7C shows a cross sectional view across elongated bore 708.

The invention claimed is:
1. A dynamic spinal stabilization device, comprising:
a plurality of pedicle screw anchors to substantially align with a corresponding plurality of vertebral bodies;
a plurality of pedicle screws corresponding to the plurality of pedicle screw anchors threadable into the plurality of vertebral bodies to connect the plurality of pedicle screw anchors to the plurality of vertebral bodies;

at least one rod coupled to and extending between the plurality of pedicle screw anchors;

an elastic material forming a resilient connection between at least one pedicle screw of the plurality of pedicle screws and the at least one rod to provide resilient movement of the at least one pedicle screw and the at least one rod with respect to one another;

at least one pedicle screw anchor of the plurality of pedicle screw anchors being elongated providing a space for the associated at least one pedicle screw of the plurality of pedicle screws to move, and the space being packed with the elastic material in contact and surrounding the associated at least one pedicle screw to provide resistance to movement of the at least one pedicle screw; and a degradable material packed into the space, and in contact and surrounding the associated at least one pedicle screw, to prevent movement for an initial period until the at least one pedicle screw fuses to at least one pedicle;

wherein a combination of the elastic material and the degradable material provide a shock absorbing effect after the initial period, during degradation of the degradable material.

2. The dynamic spinal stabilization device according to claim 1, wherein the plurality of pedicle screws are multi-axial.

3. The dynamic spinal stabilization device according to claim 1, wherein each of the pedicle screw anchors further comprises a saddle holding the rod.

4. The dynamic spinal stabilization device according to claim 3, wherein each of the pedicle screw anchors comprises a set screw threaded into the saddle to provide a seating force on the rod.

5. The dynamic spinal stabilization device according to claim 3, further comprising a spacer between the saddle holding the rod and the pedicle screw.

6. The dynamic spinal stabilization device according to claim 5, wherein the spacer comprises an air gap.

7. The dynamic spinal stabilization device according to claim 1, wherein a combination of the degradable material and the elastic material is configured to prevent movement of the at least one pedicle screw and the at least one rod with respect to one another for an initial period of time until the degradable material is at least partially absorbed, and the combination of the degradable material and the elastic material is configured to allow resilient movement of the at least one pedicle screw and the at least one rod with respect to one another after the initial period of time when the degradable material is at least partially degraded.

\* \* \* \* \*